United States Patent [19]

Chen et al.

[11] Patent Number: 5,227,564
[45] Date of Patent: Jul. 13, 1993

[54] PROCESS FOR THE PREPARATION OF TERTIARY OLEFINS

[75] Inventors: S. C. Chen, Taipei; C. C. Chu, Kaohsiung; F. S. Lin, Kaohsiung; Liang Sheu, Kaohsiung; Shing Y. Wang, Kaohsiung, all of Taiwan

[73] Assignee: Dairen Chemical Corporation, Taipei, Taiwan

[21] Appl. No.: 804,002

[22] Filed: Dec. 9, 1991

[51] Int. Cl.$^5$ .............................................. C07C 1/20
[52] U.S. Cl. .................................... 585/640; 585/639; 568/697
[58] Field of Search ............................... 585/640, 639

[56] References Cited

U.S. PATENT DOCUMENTS 4,409,421 10/1983 Herwig et al. ................... 585/833

FOREIGN PATENT DOCUMENTS 0123449 10/1984 European Pat. Off. .

Primary Examiner—Asok Pal
Assistant Examiner—P. Achutamurthy
Attorney, Agent, or Firm—Sachs & Sachs

[57] ABSTRACT

A process for the preparation of tertiary olefins by decomposition of a tertiary alkyl ether in the vapor phase in the presence of a catalyst, wherein the catalyst used is a composition of: (i) 5 to 95 percent by weight of a crystalline aluminosilicate zeolite having a silica-to-alumina mole ratio of at least about 5 and a Constraint Index of about 1 to about 12, and (ii) 95 to 5 percent by weight of a binder selected from amorphous silica, alumina, silica-alumina and mixtures thereof.

16 Claims, No Drawings

PROCESS FOR THE PREPARATION OF TERTIARY OLEFINS

BACKGROUND OF THE INVENTION

1. Field of the Invention

This invention relates to a process for the preparation of tertiary olefins from the corresponding tertiary alkyl ethers, and more particularly, to such process using an improved catalyst therein.

2. Description of the Prior Art

Tertiary olefins are important starting materials for the preparation of polymers and specialty chemicals. For example, isobutylene is used as a monomer for making elastomers such as polyisobutylene and butyl rubber, and as an intermediate for the production of isoprene, diisobutylene, tert-butyl phenol, tertbutyl amine, tert-butyl mercaptan and methyl methacrylate. Tertiary olefins usually are obtained by decomposing the corresponding tertiary alkyl ethers. For example, decomposition of methyl tertiary butyl ether (MTBE) provides isobutylene, while decomposition of tertiary amyl methyl ether (TAME) will produce isoamylene.

Several processes have been proposed for preparing tertiary olefins from tertiary alkyl ethers. For example, U.S. Pat. Nos. 4,447,668, 4,551,567, 4,570,026 and 4,751,343 disclose a process using a cation acidic exchange resin as catalyst; Japanese Patent Publication 41,882/72 discloses a process in which MTBE is decomposed using a alumina-type acidic solid catalyst having a specific surface area of at least 25 m$^2$/g; U.S. Pat. No. 4,006,198 describes a process using a catalyst composed of active alumina modified by reaction with a silicon compound; Japanese Patent Application Laid-Open Specification 2,695/80 discloses a process using a catalyst comprising silica combined with various metal oxides; Japanese Patent Application Laid-Open Specification 94,602/74 proposes a process using an active carbon catalyst; U.S. Pat. No. 3,637 889 teaches a process using a metal sulfate as a catalyst; U.S. Pat. No. 4,398,051 describes a process using a catalyst produced by calcining an aluminum compound supported on a carrier containing silicon oxides at a temperature above that at which the aluminum compound decomposes; U.S. Pat. No. 4,395,580 describes a process in which the decomposition is carried out in the presence of steam by using a catalyst comprising titanium, hafnium or zirconium supported on alumina; Japanese Patent Application Laid-Open Specification 13,734/84 describes a process in which the decomposition is carried out in the presence of steam and the catalyst comprises heteropoly acids on neutral or acidic supports; European Patent Application 118,085 relates a process using a solid phosphoric acid catalyst which has been calcined at a temperature higher than 500° C. in an inert gas; Japanese Patent Application Laid-Open Specification 106,031/87 teaches a process using niobic acid as catalyst; Japanese Patent Application Laid-Open Specification 53,739/90 teaches a process using B-containing porous glass as catalyst; Japanese Application Laid-Open Specification 53,740/90 teaches a process using tantalic acid as catalyst; U.S. Pat. No. 4,343,959 discloses a process using a catalyst obtained by calcining a silica-alumina compound at 700 to 1000° C.; U.S. Pat. No. 4,254,296 discloses a process using a catalyst system which consists of a crystalline silica having a high specific surface area which is modified with an oxide of a metallic cation; U.S. Pat. No. 4,371,725 discloses a process which is carried out in the presence of hydrogen using an acidic molecular sieve as catalyst.

These disclosed processes, however, are not entirely satisfactory for practical industrial operations for the following reasons. (1) A dimethyl ether by-product may be formed as a dehydration of two molecules of methanol itself the product of the decomposition of MTBE; accordingly the amount of alcohol recovered during the process is low. (2) Furthermore, the tertiary olefin product may dimerize, or even trimerize, reducing the yield of product. (3) The olefin also may be hydrated to the corresponding tertiary alcohol. (4) A high reaction temperature may be required; (5) The preparation of the catalyst used may be exceedingly complex, or require expensive chemicals; and (6) moreover, the catalyst life may be short and/or unstable toward steam, and/or high temperatures used during the process.

Accordingly, it is an object of this invention to provide an industrial process for the preparation of tertiary olefins by the decomposition of tertiary alkyl ethers at a high conversion and selectivity of products obtained using an improved catalyst composition which can function effectively at relatively low reaction temperatures and is stable and durable.

SUMMARY OF THE INVENTION

The present invention relates to a process for the preparation of a tertiary olefin by decomposition of the corresponding tertiary alkyl ether in the vapor phase in the presence of a catalyst, the improvement which is characterized by using a catalyst composition comprising; (i) 5 to 95 percent by weight of a crystalline aluminosilicate zeolite having a silica-to-alumina mole ratio of at least about 5 and a Constraint Index of about 1 to about 12, and (ii) 95 to 5 percent by weight of a binder selected from amorphous silica, alumina, silica-alumina, and mixtures thereof.

DETAILED DESCRIPTION OF THE INVENTION

Any suitable tertiary alkyl ether may be used in the present invention. However, tertiary alkyl ethers represented by the following general formula are ordinarily used:

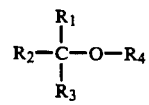

wherein R$_1$, R$_2$ and R$_3$, which may be the same or different, are alkyl groups having 1 to 4 carbon atoms, preferably 1 to 3 carbon atoms, straight chain or branched, such as a methyl, ethyl, propyl or isopropyl, and R$_4$ is an alkyl group having 1 to 6 carbon atoms, straight chain or branched, preferably methyl, ethyl, propyl or isopropyl.

Methyl tert butyl ether (MTBE) and ethyl tert-butyl ether (ETBE) are preferred tertiary alkyl ether starting materials for making isobutylene, while TAME is the preferred tertiary alkyl ether for making isoamylene.

The catalyst used in the present invention comprises a crystalline aluminosilicate zeolite having a SiO$_2$/Al$_2$O$_3$ mole ratio of at least about 5, preferably about 12 to 2000, and most preferably about 15 to 500; and a Constraint Index of about 1 to 12, as defined in U.S. Pat. No. 4,016,218 and "Journal of Catalysis" 67, 218-222 (1981).

Constraint Index (CI) values for some suitable materials are given in Table 1 below:

TABLE 1

| Catalyst | CI (at test temperature) |
| --- | --- |
| ZSM-5 | 6–8.3 (371° C.–316° C.) |
| ZSM-11 | 5–8.7 (371° C.–316° C.) |
| ZSM-12 | 2.3 (316° C.) |
| ZSM-22 | 7.3 (427° C.) |
| ZSM-23 | 9.1 (427° C.) |
| ZSM-35 | 4.5 (454° C.) |
| ZSM-38 | 2.0 (510° C.) |
| ZSM-48 | 3.5 (538° C.) |
| ZSM-50 | 2.1 (427° C.) |
| TMA-Offretite | 3.7 (316° C.) |

Crystalline aluminosilicate zeolites useful herein include those having the structure of ZSM-5, ZSM-11, ZSM-5/ZSM-11 intermediate, ZSM-12, ZSM-22, ZSM-23, ZSM-35, SAM-38, ZSM-48, ZSM-50 and similar materials, preferably ZSM-5.

ZSM-5, is described in more detail in U.S. Pat. No. 3,702,886 and Re. 29,949; ZSM-11 is described in U.S. Pat. 3,709.979; ZSM-5/ZSM-11 intermediate is described in U.S. Pat. No. 4,229,424; ZSM-12 is described in U.S. Pat. No. 3,832,449; ZSM-23 is described in U.S. Pat. No. 4,076,842; ZSM-22 is described in U.S. Pat. No. 4,556,477; ZSM-35 is described in U.S. Patent 4,016,245; ZSM-38 is described in U.S. Pat. No. 4,046,859; ZSM-48 is described in U.S. Pat. No. 4,397,827; and ZSM-50 is described is U.S. Pat. No. 4,640,829. The disclosures of these patents are hereby incorporated by reference herein.

The grain sizes of such crystalline aluminosilicate zeolite generally are within the range of about 0.01 to 40 microns, preferably 0.5 to 30 microns.

Usually the zeolite is synthesized in the form of the alkali metal salt, such as sodium salt; such zeolites are conveniently converted to the preferred hydrogen form, generally through the intermediate formation of the ammonium by ion exchange followed by calcination. Alternatively, the original alkali metal form of the zeolite, or the introduced hydrogen cations, may be replaced by ion exchange with other suitable ions of Group IB to VIII in the Periodic Table, including, for example, nickel, cadmium, copper, zinc, calcium, platinum, palladium and rare earth metals.

The zeolite content of the catalyst composition used in the present invention is about 5 to about 95 percent by weight, preferably about 40 to about 95 percent by weight, and most preferably about 60 to about 95 percent by weight, of the composition.

The binder used in the catalyst composition is selected from amorphous silica, alumina, silica-alumina, and mixtures thereof. Amorphous silica is preferred; it may be a xerogel, like Hisil or Ultrasil or similar material, and may be used alone or mixed with a dispersed silica, e.g. Ludox or silica which is precipitated before or after compositing.

The binder content of the catalyst composition suitably is about 95 to about 5 percent by weight, preferably about 60 to about 5 percent by weight, particularly preferably about 40 to about 5 percent by weight.

The catalysts composition of this invention also may include various catalytic metals, such as, copper, zinc or a metal of groups V-A (e.g. Bi), VI-B (e.g. Cr, Mo, W) or VIII (e.g. Fe, Co., Ni, Ru, Rh, Pd, Ir, and Pt) of the Periodic Table, and combinations thereof. Preferred metals are present in Group VIII of the Period Table, and may be used alone or in mixtures thereof. Particularly preferred metals are Pt and Pd, and their mixtures. These metals usually are present in amounts of about 0.01 to about 5 percent by weight, preferably about 0.02 to about 3 percent by weight, and most preferably about 0.05 to about 2 percent by weight, of the composition impregnated into the composition, ion-exchanged therein or intimately and physically admixed therewith.

The present process may be carried out in a fixed bed, fluidized bed or moving bed reactor, and, preferably, a fixed bed reactor. The reaction temperature is suitably about 100° to 400° C., preferably about 110° to 300° C.; and most preferably about 120° to 250° C. The reaction pressure suitably is about 1 to 30 atm., preferably about 1 to 15 atm. The weight hourly space velocity (WHSV) of the feed is about 0.1 to 100 1/hr, preferably 0.3 to 50 1/hr, and most preferably, to about 0.5 to 30 1/hr.

The catalyst may take any suitable form or shape, for example, a powder, an extruded pellet, granule, cylinder, tablet, sphere, microsphere, hollow cylinder or star=type and the like, without any particular limitation.

The present invention will now be described in detail with reference to the following examples without being considered as limiting the scope of the invention.

EXAMPLE 1

ZSM-5 zeolite having a silica-to-alumina mole ratio of 150 and a crystal size of 2 to 4 microns was converted to its H-form by ion-exchange under reflux in a 2.5N NH$_4$NO$_3$ solution for 4 hours at 90° C., washing, drying at 105° C. and calcining in air at 560° C. 4 hours. The HZSM-5 obtained was then composited with amorphous silica to form a catalyst composition comprising 70 wt. percent HZSM-5 and 30 wt. percent amorphous silica and extruded into cylinders of 1.5 mm diameter and 6 mm length. The catalyst was then calcined for 6 hours at 500° C.

Twenty grams of the calcined catalyst was charged into a stainless steel reactor of 23.5 mm internal diameter for the decomposition reaction:

| Reaction Conditions | |
| --- | --- |
| Feed Stock | MTBE |
| Flow Rate | 2 g/min (WHSV = 6 1/hour) |
| Temperature | 190° C. |
| Pressure | slightly above 1 atm. |

The reaction products were analyzed to give the following results:

| | Result (in Mole %) |
| --- | --- |
| Conversion | |
| MTBE | 97.20% |
| Selectivity | |
| Isobutylene | 99.55% |
| Methanol | 96.50% |
| Diisobutylene | 0.40% |
| Tert-butyl alcohol | 0.05% |
| Dimethyl ether | 3.50% |

EXAMPLE 2

The procedure of Example 1 was repeated with a zeolite having a silica-to-alumina mole ratio of 70 and an alumina binder; the catalyst composition was 40 wt% HZSM-5 and 60 wt% alumina.

Twenty grams of the calcined catalyst was charged into a stainless steel reactor of 23.5 mm internal diameter for the decomposition reaction.

| Reaction Conditions | |
| --- | --- |
| Feed Stock | TAME |
| Flow Rate | 1.5 g/min (WHSV = 4.5 l/hour) |
| Temperature | 180° C. |
| Pressure | 3 atm. |

The reaction products from the reactor were analyzed to give the following results:

| | Result (in Mole %) |
| --- | --- |
| Conversion | |
| TAME | 94.0% |
| Selectivity | |
| Isoamylene | 99.7% |
| Methanol | 97.2% |
| Diisoamylene | 0.3% |
| Tert-amyl alcohol | nil |
| Dimethyl ether | 2.8% |

EXAMPLE 3

The procedure of Example 1 was repeated with a zeolite having a silica-to-alumina mole ratio of 40 and a silica-alumina binder. The catalyst composition comprised 50 wt% HZSM-5, and 50 wt% silica-alumina.

Twenty grams of the calcined catalyst was charged in a stainless steel reactor of 23.5 mm internal diameter for the decomposition reaction.

| Reaction Conditions | |
| --- | --- |
| Feed Stock | ETBE |
| Flow Rate | 1 g/min (WHSV = 3 l/hour) |
| Temperature | 170° C. |
| Pressure | 2 atm. |

The reaction products from the reactor were analyzed to give the following results:

| | Result (in Mole %) |
| --- | --- |
| Conversion | |
| ETBE | 95.00% |
| Selectivity | |
| Isobutylene | 99.40% |
| Ethanol | 98.00% |
| Diisobutylene | 0.55% |
| Tert-butyl alcohol | 0.05% |
| Diethyl ether | 2.00% |

EXAMPLE 4

ZSM-5 zeolite having a silica-to-alumina mole ratio of 225 and a crystal size of 2 to 4 microns was converted to the H-form by ion exchange under reflux in a 2.5 N NH$_4$NO$_3$ solution for 4 hours at 90° C. followed by washing, drying at 105° C. and calcining in air at 560° C. for 4 hours. The HZSM-5 zeolite then was refluxed in 200 ml of 0.2 wt% PdCl$_2$ solution for 9 hours, filtered, washed with deionized water until no chloride could be detected in the wash, dried at 110° C., and calcined at 350° C. for 6 hours The PdZSM-5 was then composited with amorphous silica (catalyst composition—PdZSM-5 60 wt%, amorphous silica 40 wt%) and extruded into cylinders of 1.5 mm diameter and 6 mm length. The catalyst was then calcined for 4 hours at 550° C. and reduced at 500° C. with hydrogen for 4 hours.

Twenty grams of the calcined catalyst was charged into a stainless steel reactor of 23.5 mm internal diameter.

| Reaction Conditions | |
| --- | --- |
| Feed Stock | MTBE |
| Flow Rate | 4 g/min (WHSV = 12 l/hour) |
| Temperature | 220° C. |
| Pressure | 7 atm. |

The reaction products from the reactor were analyzed to give the following results:

| | Result (in Mole %) |
| --- | --- |
| Conversion | |
| MTBE | 97.50% |
| Selectivity | |
| Isobutylene | 99.05% |
| Methanol | 96.40% |
| Diisobutylene | 0.80% |
| Tert-butyl alcohol | 0.15% |
| Dimethyl ether | 3.60% |

EXAMPLE 5

The procedure of Example 4 was repeated except that the HZSM-5 was refluxed in 200 mil of 0.5% ammonium dichloroplatinate solution. The reaction conditions and the results are shown below.

| Reaction Conditions | |
| --- | --- |
| Feed Stock | ETBE |
| Flow Rate | 2 g/min (WHSV = 6.0 l/hour) |
| Temperature | 215° C. |
| Pressure | 5 atm. |

| | Result (in Mole %) |
| --- | --- |
| Conversion | |
| ETBE | 96.20% |
| Selectivity | |
| Isobutylene | 99.50% |
| Ethanol | 98.30% |
| Diisobutylene | 0.46% |
| Tert-butyl alcohol | 0.04% |
| Diethyl ether | 1.70% |

COMPARATIVE EXAMPLE 1

Twenty grams of Mordenite zeolite in the H-form having a silica-to-alumina mole ratio of 20 and a Constraint Index of 0.5, was charged into a stainless steel reactor of 23.5 mm internal diameter.

| Reaction Conditions | |
| --- | --- |
| Feed Stock | TAME |
| Flow Rate | 1 g/min (WHSV = 3.0 l/hour) |
| Temperature | 230° C. |
| Pressure | 3 atm. |

The reaction products from the reactor were analyzed with the following results:

|  | Result (in Mole %) |
| --- | --- |
| Conversion | |
| TAME | 92.1% |
| Selectivity | |
| Isoamylene | 97.2% |
| Methanol | 92.5% |
| Diisoamylene | 2.1% |
| Tert-amyl alcohol | 0.7% |
| Dimethyl ether | 7.5% |

COMPARATIVE EXAMPLE 2

Twenty grams of amorphous silica-alumina catalyst having a silica-to-alumina weight ratio of 87/13 was charged into a stainless steel reactor of 23.5 mm internal diameter.

| Reaction Conditions | |
| --- | --- |
| Feed Stock | MTBE |
| Flow Rate | 1 g/min (WHSV = 3.0 l/hour) |
| Temperature | 210° C. |
| Pressure | 5 atm. |

The reaction products were analyzed to give the following results:

|  | Result (in Mole %) |
| --- | --- |
| Conversion | |
| MTBE | 96.0% |
| Selectivity | |
| Isoamylene | 95.2% |
| Methanol | 91.3% |
| Diisoamylene | 4.0% |
| Tert-butyl alcohol | 0.8% |
| Dimethyl ether | 8.7% |

What is claimed is:

1. A process for the production of a tertiary olefin and an alcohol by decomposition of the corresponding tertiary alkyl ether in the vapor phase at a temperature of about 120° to about 300° C. and a pressure of about 1 to about 10 atmospheres in the presence of a catalyst composition comprising:
   (i) 5 to 95 percent by weight of a crystalline alumina silicate zeolite having a silica-to-alumina mole ratio of about 15 to about 500 and a Constraint Index of about 1 to about 12, and
   (ii) 95 to 5 percent by weight of a binder selected from amorphous silica, alumina, silica-alumina, and mixtures thereof, and wherein:
   conversion of such tertiary alkyl ether is at least 94 mole %, and selectivity towards production of said tertiary olefin is at least 99 mole % and towards production of said alcohol is at least 96 mole %.

2. A process according to claim 1 wherein the crystalline aluminosilicate zeolite is ZSM-5, ZSM-11, ZSM-5/ZSM-11 intermediate, ZSM-12, ZSM-22, ZSM-23, ZSM-35, ZSM-38, ZSM-48 or ZSM-50 and mixtures thereof.

3. A process according to claim 2 wherein said zeolite is ZSM-5 or HZSM-5.

4. A process according to claim 1 wherein the binder is amorphous silica.

5. A process according to claim 1 wherein the catalyst also includes a catalytic metal of Group VIII of the Periodic Table.

6. A process according to claim 5 wherein the catalytic metal is Pt or Pd, or mixtures thereof.

7. A process according to claim 1 wherein the tertiary alkyl ether has the formula:

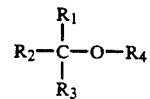

wherein $R_1$, $R_2$ and $R_3$ is the same or different, are alkyl groups straight or branched chain having 1 to 4 carbon atoms, and $R_4$ is an alkyl group, straight or branched chain, having from 1 to 6 carbon atoms.

8. A process according to claim 7 wherein $R_1$, $R_2$ and $R_3$ are alkyl groups having from 1 to 2 carbon atoms, and $R_4$ is an alkyl group having from 1 to 4 carbon atoms.

9. A process according to claim 1 wherein the tertiary olefin is isobutylene.

10. A process according to claim 1 wherein said tertiary olefin is isoamylene.

11. A process according to claim 7 wherein the tertiary alkyl ether is methyl tertiary butyl ether, methyl tertiary amyl ether, ethyl tertiary butyl ether, or mixtures thereof.

12. A process according to claim 11 wherein said the tertiary alkyl ether is methyl tertiary butyl ether.

13. A process according to claim 11 wherein the tertiary alkyl ether is methyl tertiary amyl ether.

14. A process according to claim 1 wherein the reaction is carried out in a fixed, fluidized or moving bed reactor.

15. A process according to claim 14 wherein said the reaction is carried out in a fixed bed reactor.

16. A process according to claim 2 wherein:
   (i) the zeolite comprises 40 to 95 percent by weight, and
   (ii) the binder comprises 60 to 5 percent by weight of the catalyst composition.

* * * * *

UNITED STATES PATENT AND TRADEMARK OFFICE
CERTIFICATE OF CORRECTION

PATENT NO. : 5,227,564
DATED : July 13, 1993
INVENTOR(S) : S.C. Chen, C.C. Chu, F.S. Lin, Liang Shu, Shiang Y. Wang It is certified that error appears in the above—identified patent and that said Letters Patent is hereby corrected as shown below:

Column 4, line 21; delete "star=type" and insert therefor --star-type--.

Column 6, line 33; delete "mil" and insert therefor --ml--.

Column 7, line 34; delete "Isoamylene" and insert therefor --Isobutylene--.

Column 7, line 36; delete "Diisoamylene" and insert therefor --Dissobutylene--.

Signed and Sealed this

Fifth Day of April, 1994

Attest:

BRUCE LEHMAN

*Attesting Officer*     Commissioner of Patents and Trademarks